US00PP16508P2

(12) United States Plant Patent
Trees

(10) Patent No.: US PP16,508 P2
(45) Date of Patent: May 9, 2006

(54) ***GERANIUM* PLANT NAMED 'BALDESCARIM'**

(50) Latin Name: *Pelargonium×hortorum*
Varietal Denomination: Baldescarim

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 184 days.

(21) Appl. No.: 11/016,299

(22) Filed: Dec. 17, 2004

(51) Int. Cl.
*A01H 5/00* (2006.01)

(52) U.S. Cl. ..... Plt./330
(58) Field of Classification Search ..... Plt./330
See application file for complete search history.

*Primary Examiner*—Kent Bell
(74) *Attorney, Agent, or Firm*—Wood, Phillips, Katz, Clark & Mortimer

(57) ABSTRACT

A new and distinct cultivar of *Geranium* plant named 'Baldescarim', characterized by its semi-double red-colored flowers, dark green-colored foliage, and vigorous, upright, and mounded growth habit.

2 Drawing Sheets

Latin name of genus and species of plant claimed: *Pelargonium×hortorum.*
Variety denomination: 'Baldescarim'.

BACKGROUND OF THE INVENTION

The present invention relates to a new and distinct cultivar of *Geranium* plant botanically known as *Pelargonium× hortorum* and hereinafter referred to by the cultivar name 'Baldescarim'.

The new cultivar originated in a controlled breeding program in Arroyo Grande, Calif., during January 2001. The objective of the breeding program was the development of *Geranium* cultivars with a vigorous, upright and mounded growth habit, dark green-colored foliage, and new and unique flower coloration.

The female (seed) parent of the new cultivar was 'Fislet', U.S. Plant Pat. No. 12,453, characterized by its large umbels and lightly zoned foliage. The male (pollen) parent of the new cultivar was 'Fisfire', U.S. Plant Pat. No. 12,489, characterized by its small umbels and heavily zoned foliage. The new *Geranium* was discovered and selected by the inventor as a single flowering plant within the progeny of the above stated cross-pollination during July 2002 at Arroyo Grande, Calif.

Asexual reproduction of the new cultivar by terminal stem cuttings taken since July 2002 at Arroyo Grande, Calif. and West Chicago, Ill., has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Baldescarim' as a new and unique cultivar of *Geranium* plant:

1. Semi-double red-colored flowers.
2. Dark green-colored foliage with distinct darker green-colored zone.
3. Vigorous, upright, and mounded growth habit.

Plants of the new cultivar differ from plants of the female primarily in umbel size and foliage color and from plants of the male parent primarily in umbel size and foliage color.

Of the many commercially available *Geranium* cultivars known to the inventor, the most similar in comparison to the new cultivar is 'Fislet' (U.S. Plant Pat. No. 12,453). However, in side by side comparisons, plants of the new cultivar differed from plants of 'Fislet' in the following characteristics:

1. Plants of the new cultivar have fewer flowers per umbel than plants of 'Fislet'.
2. Plants of the new cultivar exhibit a more distinct leaf zonation than plants of 'Fislet'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldescarim'. The plants were grown for 8 weeks in a greenhouse in West Chicago, Ill.

DETAILED BOTANICAL DESCRIPTION

Figure 1:
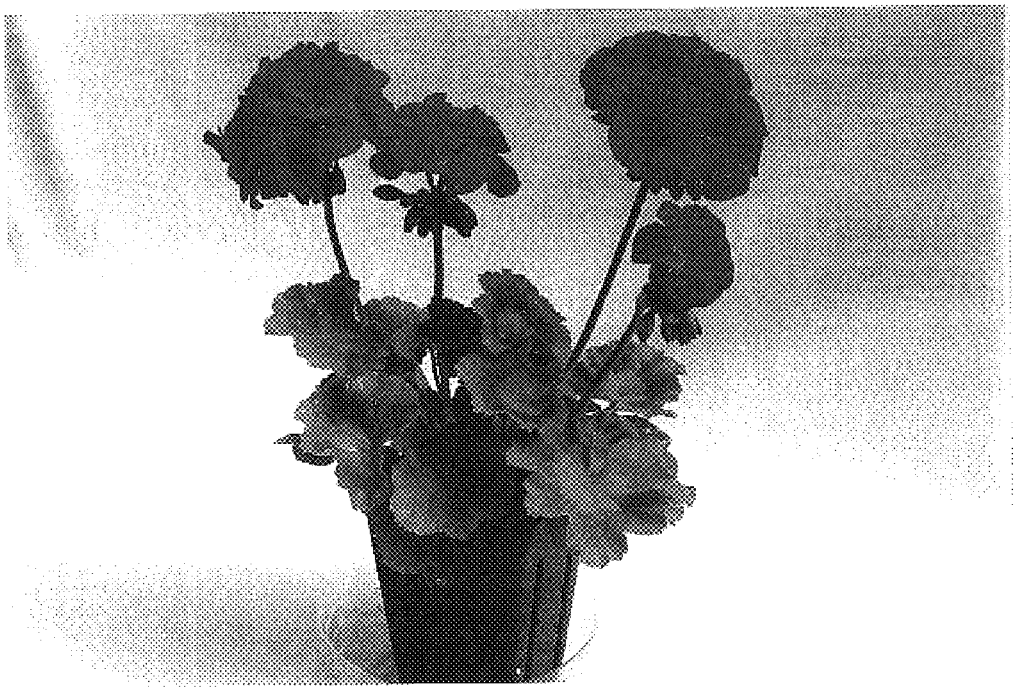
FIG. 1 illustrates a side view of the overall growth and flowering habit of 'Baldescarim'.
Figure 2:
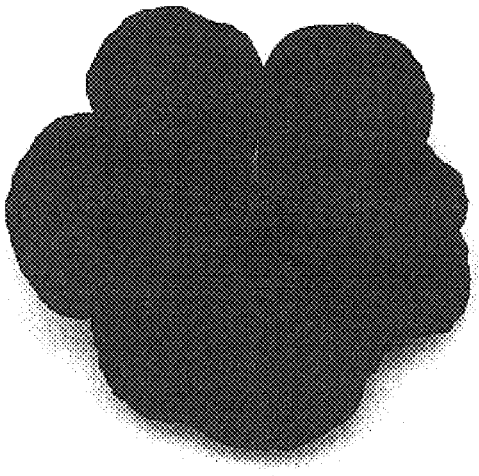
FIG. 2 illustrates a close-up view of a single flower of 'Baldescarim'.
Figure 3:
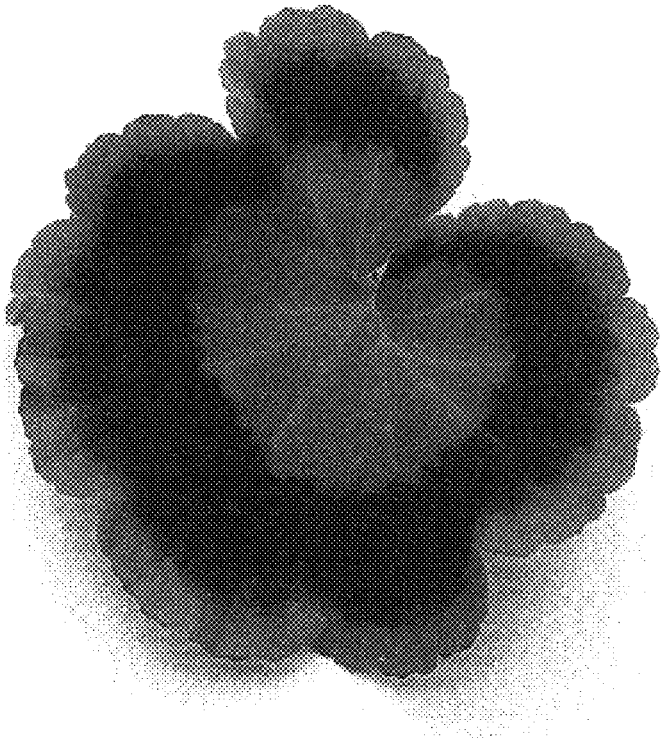
FIG. 3 illustrates a close-up view of a single leaf of 'Baldescarim'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Nov. 14, 2004 between 3:00 and 4:00 p.m. under natural light conditions, in West Chicago, Ill.

The following descriptions and measurements describe plants produced from cuttings taken from stock plants and grown in a double polycarbonate-covered greenhouse in West Chicago, Ill. under conditions comparable to those used in commercial practice. The plants were grown at West Chicago, Ill. in 10 cm pots for 8 weeks utilizing a soilless growth medium. Greenhouse temperatures were maintained at approximately 65°–70° F. (18°–21° C.) during the day and approximately 60°–65° F. (15°–18° C.) during the night. Greenhouse light levels of 4,000–6,000 footcandles were maintained during the day.

Botanical classification: *Pelargonium×hortorum* cultivar Baldescarim.

Parentage:

*Female parent.*—'Fislet', U.S. Plant Pat. No. 12,453.

*Male parent.*—'Fisfire', U.S. Plant Pat. No. 12,489.

Propagation:

*Type cutting.*—Terminal stem.

*Time to initiate roots.*—Approximately 10 to 14 days.

*Time to produce a rooted cutting.*—Approximately 21 to 28 days.

*Root description.*—Fibrous.

*Rooting habit.*—Freely branching.

Plant description:

*Crop time.*—Approximately 8–9 weeks from a rooted cutting.

*Growth habit and general appearance.*—Vigorous, upright and mounded.

*Size.*—Height from soil level to top of plant plane: Approximately 20.7 cm. Width/area of spread: Approximately 31.8 cm.

*Branching habit.*—Freely basal branching. Approximately 4 branches per plant.

*Branch.*—Length: Approximately 7.2 cm. Diameter: Approximately 7.7 mm. Texture: Hirsute. Color: 144B. Internode length at center of branch: Approximately 1.2 cm.

*Foliage.*—Number of leaves per lateral branch: Approximately 9. Form: Simple. Arrangement: Alternate. Shape: Reniform. Margin: Crenate. Apex: Rounded. Base: Cordate, open. Venation pattern: Palmate. Length of mature leaf: Approximately 4.4 cm. Width of mature leaf: Approximately 7.8 cm. Texture of upper surface: Densely pubescent. Texture of lower surface: Moderately pubescent with dense pubescence along veins. Color of mature foliage: Upper surface: Slightly more yellow than 137A with veins of N144C and zone of 200A at outer edge. Color of mature foliage: Lower surface: 137C with venation of N145C. Petiole length: Approximately 9.8 cm. Petiole diameter: Approximately 2.3 mm. Petiole Texture: Moderately pubescent on both upper and lower surface. Petiole color: 144A.

Flowering description:

*Flowering habit.*—'Baldescarim' is freely flowering under outdoor growing conditions with substantially continuous blooming from spring through autumn and year round in greenhouse environment.

*Time to first flower.*—Approximately 8 weeks after planting of rooted cutting.

*Lastingness of individual bloom.*—Approximately 5–7 days.

Inflorescence description:

*Type.*—Hemispherical umbel. Position: Above foliage. Number of open umbels at any one time: Approximately 3. Number of developing umbels at any one time: Approximately 2. Umbel diameter: Approximately 13.3 cm. Umbel height/depth: Approximately 8.9 cm. Number of flowers per umbel: Approximately 27.

*Peduncle.*—Strong, erect. Length: Approximately 14.7 cm. Diameter: Approximately 3.2 mm. Texture: Densely glandular pubescent. Gland color: Transparent. Color: 144A.

Flower description:

*Bud rate of opening.*—Generally takes 3–5 days for bud to progress from first color to fully open flower.

*Bud just before opening.*—Shape: Oval. Length: Approximately 1.1 cm. Diameter: Approximately 8 mm. Petal color: 40A. Sepal color: 143B.

*Corolla.*—Form: Semi-double. Shape: Round, slightly cupped. Diameter/Width: Approximately 4.9 cm. Depth: Approximately 1.5 cm. Fragrance: None.

*Petals/petaloids.*—Quantity: Approximately 8 petals and 7 irregular shaped petaloids per flower. Arrangement: Imbricate. Shape: Obovate. Apex: Obtuse. Base: Attenuate. Margin: Entire. Texture of upper and lower surface: Glabrous. Petal length: Approximately 2.8 cm. Petal width: Approximately 2.4 cm. Color of upper surface of all fully opened petals/petaloids: Closest to but deeper than 42A. Color of lower surface all fully open petals/petaloids: 43C.

*Pedicel.*—Strength: Strong. Angle: Erect to slightly acute. Length: Approximately 2.9 cm. Diameter: Approximately 1.2 mm. Texture: Densely pubescent. Color: 144B with overlay of 183B.

*Sepals.*—Quantity per flower: 5. Shape: Lanceolate. Tip: Acuminate. Base: Truncate. Margin: Entire. Sepal length: 1.2 cm. Width of largest sepal: 4 mm. Width of smallest sepal: 2.7 mm. Texture of upper/inner surface: Glabrous. Texture of lower/outer surface: Densely pubescent. Color: Upper and lower surface: 143B with overlay of 183B at base.

*Reproductive organs.*—Androecium: Anther quantity: Approximately 3–4 fertile anthers per flowers. Anther shape: Elliptic. Anther length: Approximately 2 mm. Anther color: N57C. Pollen amount: Moderate. Pollen color N25B. Gynoecium: Pistil quantity: One per flower. Pistil length: Approximately 1 cm. Stigma shape: 5 pointed star. Stigma length: 2 mm. Stigma color: 46B. Style length: 3 mm. Style color: 46B. Ovary length: 5 mm. Ovary diameter: 2 mm. Ovary texture: Sericeous. Ovary color: 143A.

Seed and fruit production: Neither seed nor fruit production has been observed.

Disease and pest resistance: Resistance to pathogens and pests common to *geraniums* has not been observed.

What is claimed is:

1. A new and distinct cultivar of *Geranium* plant named 'Baldescarim', substantially as herein shown and described.

* * * * *